(12) United States Patent
Kariniemi et al.

(10) Patent No.: US 9,427,304 B2
(45) Date of Patent: Aug. 30, 2016

(54) MULTI-LAYER DEVICE WITH GAP FOR TREATING A TARGET SITE AND ASSOCIATED METHOD

(75) Inventors: Ryan Kariniemi, Cokato, MN (US); Matthew C. Heidner, Maple Grove, MN (US); John C. Oslund, Blaine, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 674 days.

(21) Appl. No.: 12/258,899

(22) Filed: Oct. 27, 2008

(65) Prior Publication Data

US 2010/0106235 A1    Apr. 29, 2010

(51) Int. Cl.
| | |
|---|---|
| *A61F 2/06* | (2013.01) |
| *A61F 2/07* | (2013.01) |
| *A61F 2/95* | (2013.01) |
| *A61F 2/89* | (2013.01) |

(52) U.S. Cl.
CPC .. *A61F 2/07* (2013.01); *A61F 2/89* (2013.01); *A61F 2/95* (2013.01); *A61F 2220/005* (2013.01); *A61F 2220/0058* (2013.01)

(58) Field of Classification Search
CPC .............. A61F 2/86; A61F 2/84; A61F 2/07; A61F 2220/005; A61F 2/89; A61F 2200/0058; A61F 2/95
USPC ........................ 623/1.11–1.54; 606/195, 200
See application file for complete search history.

(56) References Cited

U.S. PATENT DOCUMENTS

| | | | | |
|---|---|---|---|---|
| 4,086,665 | A | | 5/1978 | Poirier |
| 4,416,028 | A | * | 11/1983 | Eriksson et al. ............ 623/1.38 |
| 5,380,328 | A | * | 1/1995 | Morgan ........................ 606/70 |
| 5,383,925 | A | * | 1/1995 | Schmitt ...................... 623/1.53 |
| 5,527,353 | A | * | 6/1996 | Schmitt ...................... 623/1.44 |
| 5,562,725 | A | * | 10/1996 | Schmitt et al. ............. 623/1.53 |
| 5,749,880 | A | * | 5/1998 | Banas et al. ................. 606/198 |
| 5,800,510 | A | * | 9/1998 | Schmitt ..................... 623/23.72 |
| 5,858,556 | A | * | 1/1999 | Eckert et al. ................ 428/586 |
| 5,911,753 | A | * | 6/1999 | Schmitt .......................... 600/36 |
| 6,099,557 | A | * | 8/2000 | Schmitt ........................ 623/1.1 |
| 6,124,523 | A | * | 9/2000 | Banas et al. ................ 623/1.15 |
| 6,217,609 | B1 | * | 4/2001 | Haverkost .................. 623/1.22 |
| 6,221,099 | B1 | * | 4/2001 | Andersen et al. .......... 623/1.15 |
| 6,245,099 | B1 | * | 6/2001 | Edwin et al. ............... 623/1.13 |
| 6,264,689 | B1 | * | 7/2001 | Colgan et al. .............. 623/1.22 |
| 6,273,917 | B1 | | 8/2001 | Inoue |
| 6,331,191 | B1 | * | 12/2001 | Chobotov ................... 623/1.44 |
| 6,342,068 | B1 | * | 1/2002 | Thompson .................. 623/1.53 |
| 6,537,310 | B1 | * | 3/2003 | Palmaz et al. .............. 623/1.13 |
| 6,589,468 | B1 | * | 7/2003 | Schmitt ......................... 264/257 |
| 6,616,617 | B1 | * | 9/2003 | Ferrera et al. ............... 600/585 |

(Continued)

*Primary Examiner* — Amy R Weisberg
(74) *Attorney, Agent, or Firm* — Armstrong Teasdale, LLLP

(57) ABSTRACT

A medical device includes a multi-layered structure comprising an inner layer disposed within an outer layer, wherein each of the inner and outer layers has respective inner and outer surfaces. The multi-layered structure further comprises at least offset located between the inner and outer layers or formed in the inner and/or outer layers to define at least one gap therebetween such that a majority of the outer surface of the inner layer is spaced apart from the inner surface of the outer layer. The multi-layered structure is configured to be deployed within a lumen such that at least a portion of the outer layer is configured to engage the lumen and the at least one gap is configured to promote thrombosis between the inner and outer layers.

22 Claims, 3 Drawing Sheets

(56) References Cited

U.S. PATENT DOCUMENTS

| | | | |
|---|---|---|---|
| 6,814,753 B2* | 11/2004 | Schmitt | 623/1.44 |
| 6,827,711 B2* | 12/2004 | Sunseri | 604/509 |
| 6,849,085 B2* | 2/2005 | Marton | 623/1.13 |
| 6,926,735 B2* | 8/2005 | Henderson | 623/1.42 |
| 7,073,504 B2* | 7/2006 | Callister et al. | 128/831 |
| 7,300,457 B2* | 11/2007 | Palmaz | 623/1.13 |
| 7,396,363 B2* | 7/2008 | Frid | 623/1.15 |
| 7,491,226 B2* | 2/2009 | Palmaz et al. | 623/1.13 |
| 7,530,988 B2* | 5/2009 | Evans et al. | 606/195 |
| 7,598,652 B2* | 10/2009 | Kornbluh et al. | 310/309 |
| 7,641,680 B2* | 1/2010 | Palmaz et al. | 623/1.13 |
| 7,736,687 B2* | 6/2010 | Sims et al. | 427/2.1 |
| 7,744,644 B2* | 6/2010 | Weber et al. | 623/1.42 |
| 7,758,892 B1* | 7/2010 | Chen et al. | 424/497 |
| 2002/0040237 A1 | 4/2002 | Lentz et al. | |
| 2002/0123790 A1* | 9/2002 | White et al. | 623/1.14 |
| 2003/0153971 A1* | 8/2003 | Chandrasekaran | 623/1.15 |
| 2004/0054406 A1* | 3/2004 | Dubson et al. | 623/1.39 |
| 2004/0176740 A1* | 9/2004 | Chouinard | 604/527 |
| 2005/0033418 A1* | 2/2005 | Banas et al. | 623/1.49 |
| 2005/0165468 A1* | 7/2005 | Marton | 623/1.13 |
| 2005/0171569 A1* | 8/2005 | Girard et al. | 606/193 |
| 2005/0187604 A1* | 8/2005 | Eells et al. | 623/1.13 |
| 2005/0209633 A1* | 9/2005 | Callister et al. | 606/200 |
| 2005/0228434 A1* | 10/2005 | Amplatz et al. | 606/200 |
| 2005/0261760 A1 | 11/2005 | Weber | |
| 2005/0267570 A1* | 12/2005 | Shadduck | 623/1.44 |
| 2007/0168019 A1* | 7/2007 | Amplatz et al. | 623/1.18 |
| 2007/0244569 A1* | 10/2007 | Weber et al. | 623/23.75 |
| 2007/0265656 A1 | 11/2007 | Amplatz et al. | |
| 2008/0200945 A1* | 8/2008 | Amplatz et al. | 606/195 |
| 2009/0062841 A1* | 3/2009 | Amplatz et al. | 606/200 |
| 2009/0082803 A1* | 3/2009 | Adams et al. | 606/213 |
| 2009/0099647 A1* | 4/2009 | Glimsdale et al. | 623/1.35 |
| 2009/0187240 A1* | 7/2009 | Clerc et al. | 623/1.17 |
| 2009/0209855 A1* | 8/2009 | Drilling et al. | 600/435 |
| 2009/0210047 A1* | 8/2009 | Amplatz et al. | 623/1.12 |
| 2009/0210048 A1* | 8/2009 | Amplatz et al. | 623/1.13 |
| 2010/0023046 A1* | 1/2010 | Heidner et al. | 606/191 |
| 2010/0023048 A1* | 1/2010 | Mach | 606/200 |
| 2010/0036475 A1* | 2/2010 | Castaneda | 623/1.13 |
| 2010/0154197 A1* | 6/2010 | Palmaz et al. | 29/557 |
| 2011/0087146 A1* | 4/2011 | Ryan et al. | 604/8 |

* cited by examiner

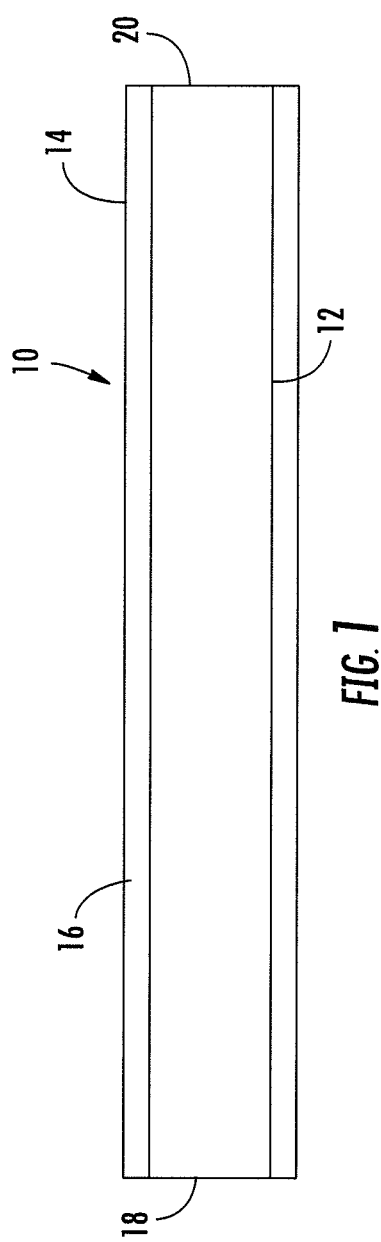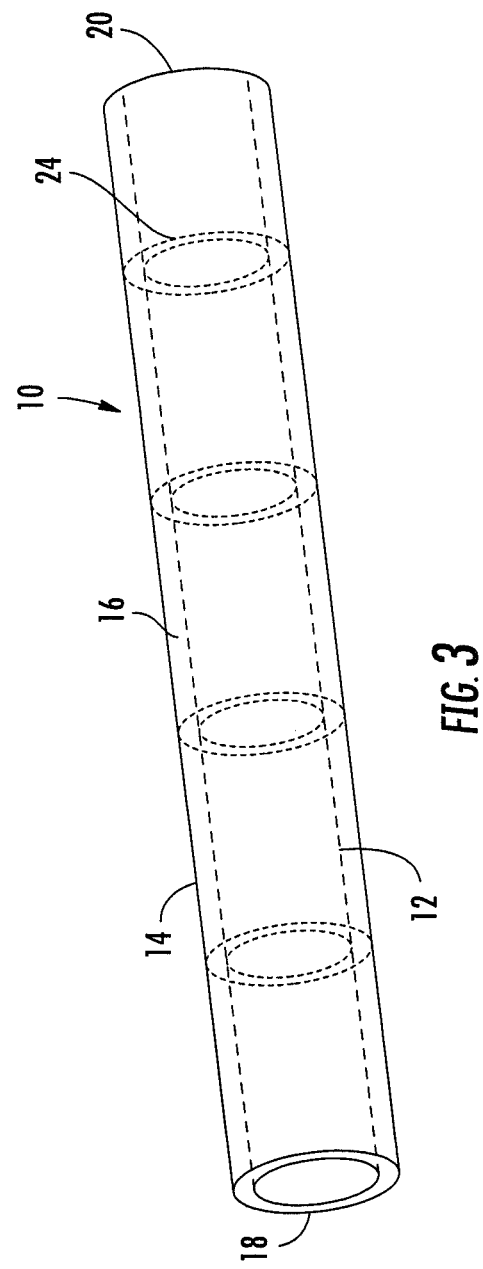

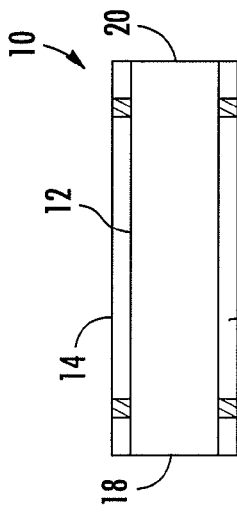
FIG. 2
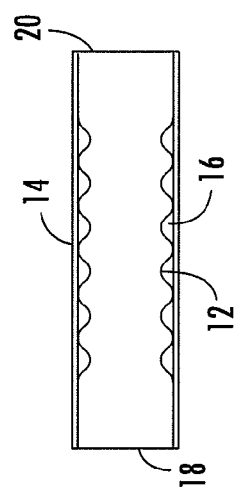
FIG. 6
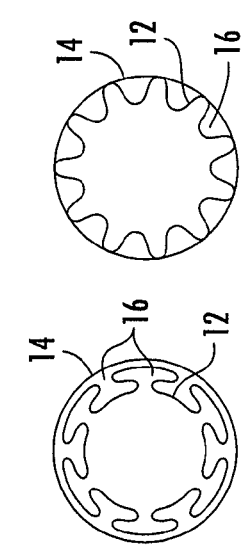
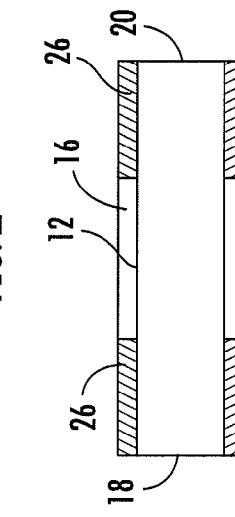
FIG. 4
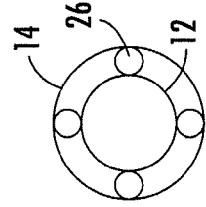
FIG. 5
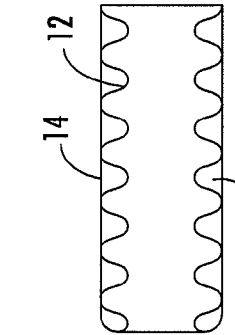
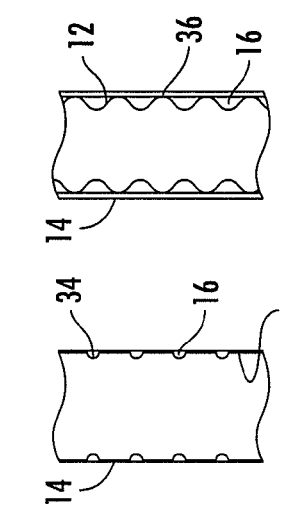
FIG. 10
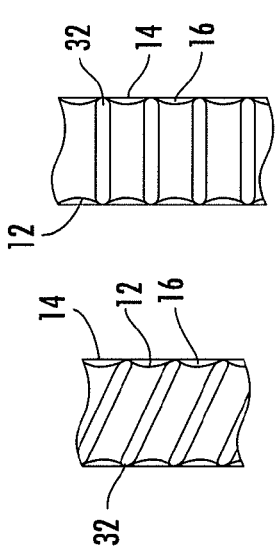
FIG. 8
FIG. 7
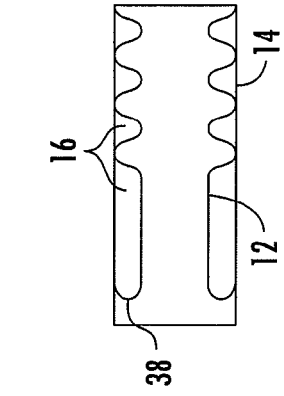

MULTI-LAYER DEVICE WITH GAP FOR TREATING A TARGET SITE AND ASSOCIATED METHOD

BACKGROUND OF THE INVENTION

1) Field of the Invention

The present invention relates to medical devices and, in particular, to a medical device for treating a target site within the body, such as a vascular abnormality, that includes multiple layers and one or more gaps between layers for more effectively treating the target site.

2) Description of Related Art

An aortic aneurysm is a weak area in the aorta, the main blood vessel that carries blood from the heart to the rest of the body. A common aneurysm is the abdominal aortic aneurysm ("AAA"), which may be caused by arteriosclerosis. As blood flows through the aorta, the weak vessel wall thins over time and expands like a balloon and can eventually burst if the vessel wall gets too thin. Most commonly, aortic aneurysms occur in the portion of the vessel below the renal artery origins. The aneurysm may be located in the vessels supplying the hips and pelvis, including the iliac arteries.

Rather than performing surgery to repair an aneurysm, vascular surgeons may install an endovascular stent graft delivered to the site of the aneurysm using elongated catheters. A stent graft can be used for a variety of conditions involving the blood vessels, but most commonly is used to exclude an aneurysm. The stent graft may be delivered to a location bridging the aneurysm, at which point the stent graft is deployed and expanded to approximately the normal diameter of the aorta at that location. Over time, the stent graft becomes endothelialized and the space between the outer wall of the stent graft and the aneurysm ultimately fills with clotted blood, which prevents the aneurysm from growing further since the stent graft bypasses (excludes) the aneurysm and prohibits systematic pressure and flow on the weakened segment of the lumen.

Depending on where the aneurysm is in relation to other branch vessels, different design variations may be needed. For example, in treating an AAA, the stent graft should be placed so as not to exclude blood flow through the renal arteries which branch off from the abdominal aorta. Moreover, the stent graft should be anchored within the lumen to reduce the incidence of migration, such as by promoting endothelialization or fixation with the lumen. Endoleaks may occur as a result of blood flowing around the stent, which may result in further weakening of the site of the aneurysm.

Medical devices, such as multi-layered occluders and stent grafts, have also been developed in order to occlude or exclude vascular abnormalities such as aneurysms. For example, the medical devices may include multiple layers of coaxially disposed layers of material that are configured to substantially slow the flow of blood and facilitate thrombosis. The idea is that having a greater surface area using a multi-layered device may speed clot formation in comparison to single layer devices and eliminate the need for an additional material such as a polyester fabric often included in single layer devices.

Despite these improvements in occluding vascular abnormalities, there is needed a multi-layer device that is capable of more effectively treating various target sites. Moreover, there is a need for a medical device that may be easily delivered and adequately anchored at the target site. In addition, there is a need for a medical device that may be delivered to a target site that is less traumatic to the vasculature and that may be used to prophylactically treat various conditions that may be in more difficult to reach anatomy. There is additionally a need for medical device that may promote thrombosis to occlude and/or exclude an aneurysm or other vascular abnormality.

BRIEF SUMMARY OF THE INVENTION

Embodiments of the present invention may provide improvements over the prior art by, among other things, providing medical devices and methods for treating a target site within the body. For example, one embodiment provides a medical device (e.g., a stent graft) for treating a target site, wherein the medical device includes a multi-layered structure comprising an inner layer disposed within an outer layer. The layers are spaced apart from one another over a majority of their adjacent surface area by at least one offset to define at least one gap between the inner and outer layers. The multi-layered structure is configured to be deployed within a lumen such that at least a portion of the outer layer is configured to engage the lumen and the at least one gap is configured to promote thrombosis between the inner and outer layers. The multi-layered structure may include an expanded heat set configuration and may be configured to be constrained to a smaller diameter than the expanded heat set configuration for delivery within a catheter. According to one embodiment, the multi-layered structure is configured to engage the lumen upstream and downstream of an aneurysm. The multi-layered structure could also be tubular in configuration.

According to various aspect of the medical device, the inner and outer layers comprise an occlusive material or a plurality of layers of braided strands (e.g., an elastic metallic alloy). The inner layer may be coaxially disposed within the outer layer. There may be a plurality of gaps defined between the proximal and distal ends of the multi-layered structure. Furthermore, the at least one offset may be a spacer, such as a tube or annular ring, that may be collapsible. The at least one offset may be a surface distortion formed in the surface of one or both layers to space apart a substantial portion of the adjacent layer's surface area. For example, the surface distortion may be corrugations or flutes formed in the outer surface of the inner layer or the inner surface of the outer layer. Additional aspects of the medical device include a multi-layered structure having a plurality of offsets positioned between the inner and outer layers. The plurality of offsets may include a plurality of surface distortions formed in the inner and/or outer layers, wherein the inner layer is disposed within the outer layer in an overlying relationship so as to define a plurality of gaps therebetween.

An additional embodiment of the present invention provides a method for treating a vascular abnormality in a lumen. The method includes positioning a medical device within a catheter, wherein the medical device includes a multi-layered structure comprising an inner layer and an outer layer and at least one offset positioned between the inner and outer layers or formed in the inner and/or outer layers such that the inner and outer layers are spaced apart from one another over a majority of their adjacent surface area to define at least one gap therebetween. The method further includes delivering the medical device proximate to the vascular abnormality in the lumen and deploying the medical device such that at least a portion of the outer layer is configured to engage the lumen and the at least one gap is configured to promote thrombosis between the inner and outer layers.

Variations of the method include deploying the medical device such that the medical device engages the lumen upstream and downstream of an aneurysm. The positioning step may include constraining the medical device, such as by elongating the medical device, to a smaller diameter than an expanded heat set configuration. The deploying step may include deploying the medical device such that the medical device is configured to self expand from the constrained smaller diameter and return to its expanded heat set configuration. In addition, the deploying step may include deploying the outer layer within the lumen and then deploying the inner layer within the outer layer. The positioning step may include positioning the medical device within a catheter such that the inner and outer layers are in axial alignment with one another.

BRIEF DESCRIPTION OF THE SEVERAL VIEWS OF THE DRAWINGS

Figure 15:
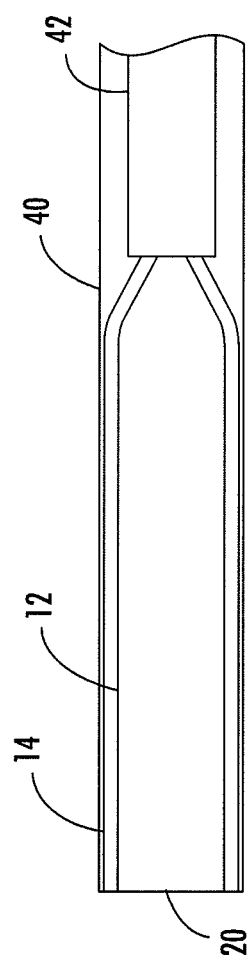
Figure 16:
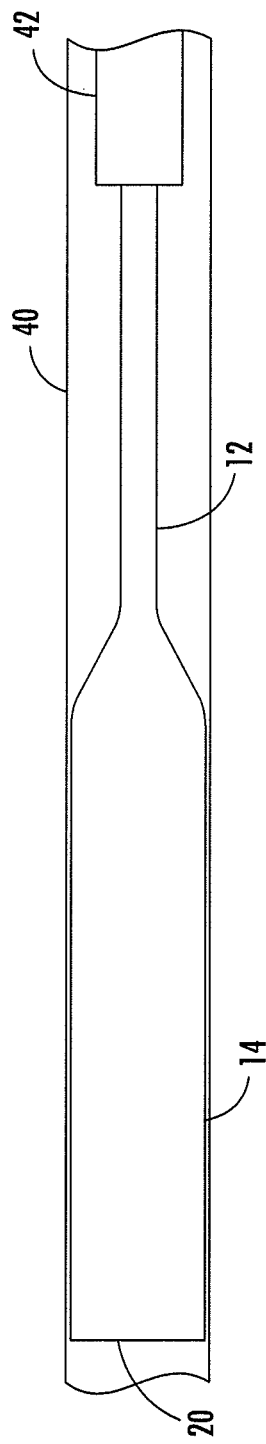

Having thus described the invention in general terms, reference will now be made to the accompanying drawings, which are not necessarily drawn to scale, and wherein:

FIG. 1 illustrates a side cross-sectional view of a stent graft according to one embodiment of the present invention;

FIGS. 2 and 4 show side cross-sectional views of stent grafts having a plurality of offsets according to additional embodiments of the present invention;

FIG. 3 depicts a perspective view of a stent graft having a plurality of offsets according to one embodiment of the present invention;

FIG. 5 illustrates an end view of a stent graft having a plurality of offsets according to an embodiment of the present invention;

FIG. 6 illustrates a side cross-sectional view of a stent graft according to one embodiment of the present invention;

FIGS. 7-9 illustrate side cross-sectional views of stent grafts having a plurality of flutes according to additional embodiments of the present invention;

FIG. 10 depicts a side cross-sectional view of a stent graft having a corrugated inner layer according to one embodiment of the present invention;

FIG. 11 is an end view of a stent graft having a plurality of longitudinal offsets according to an embodiment of the present invention;

FIG. 12 is an end view of a stent graft having a plurality of longitudinal offsets according to another embodiment of the present invention;

FIG. 13 is a partial cross-sectional view of an end graft having an everted portion defining a plurality of offsets according to one embodiment of the present invention;

FIG. 14 is a partial cross-sectional view of an end graft having one end everted to define an offset according to another embodiment of the present invention;

FIG. 15 illustrates a side view of a delivery system for delivering a stent graft according to one embodiment of the present invention; and FIG. 16 depicts a side view of a delivery system for delivering a stent graft according to one embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site within the body, such as a stent graft for excluding various vascular abnormalities, which may include, for example, excluding an aneurysm. The device may also be used as an occluder, a flow restrictor or a shunt, filter or other type of device for placement in the vascular system, as well as a graft for lining a lumen of a vessel. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a lesion, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, an appendage, or the like.

As explained in further detail below, a medical device according to one embodiment of the present invention includes a medical device such as a stent graft for treating a target site, wherein the stent graft includes a multi-layered structure having inner and outer layers. At least one offset may be located between the inner and outer layers or may be a radially projected distortion of a portion of the surface of the inner and/or outer layers to define at least one gap therebetween comprising a majority of the adjacent layer surfaces. The at least one gap is configured to promote thrombosis between the inner and outer layers, such as by increasing turbulence in and around the gap to facilitate thrombus formation and collection of thrombus in the gap to thereby further occlude or exclude the lumen such that blood flow into the aneurysm is substantially or totally eliminated but flow through the vessel is maintained.

According to one embodiment of the present invention for forming a medical device of the invention, the device includes a braided fabric formed of a plurality of wire strands having a predetermined relative orientation with respect to one another. Moreover, the device may comprise one or more layers of braided fabric or occlusive material such that the device may be a variety of occluding materials capable of at least partially inhibiting blood flow therethrough in order to facilitate the formation of thrombus and epithelialization around the device. Each layer may be a metallic material, a polymeric material, or a combination of such materials.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

The device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period. For instance, occlusion may be clinically represented by injecting a contrast media into the upstream lumen of the device and if little or no contrast media flows through the device wall after a predetermined period of time, then the position and occlusion of the device is adequate as would be recognized by one of ordinary skill in the art.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. It is also understood that the device may comprise various materials and combinations of materials other than Nitinol that have elastic properties, such as spring stainless steel, alloys such as Elgiloy®, Hastelloy®, CoCrNi alloys (e.g., trade name Phynox), MP35N®, CoCrMo alloys, or polymeric materials. Depending on the individual material selected, the wire strand diameter, number of wire strands and pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One may heat set, solder, braze, weld, coat, glue, clamp, tie or otherwise affix the ends of the desired length together. According to one embodiment, each layer of the device may comprise 36-144 wire strands ranging in diameter from about 0.001 to 0.006 in. formed of a shape memory alloy, such as Nitinol, that are braided so as to define fenestrations with an area of about 0.00015 to 0.015 sq. in., which are sufficiently small so as to slow the blood flow through the wall of the device and to facilitate thrombus formation thereon. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element may be selected to deform the fabric into substantially the shape of the desired medical device when unconstrained. Once the molding element is assembled with the metal fabric generally conforming to a molding surface of that element, the fabric may be subjected to a heat treatment while it remains in contact with that molding surface. After the heat treatment, the fabric is removed from contact with the molding element and will substantially retain its heat-set shape in a deformed state. As explained in further detail below in conjunction with the illustrated embodiments, different configurations of devices may be formed and heat set for various locations within the body.

Those skilled in the art will appreciate that in order to speed up the occlusion of the vessel or the exclusion of an aneurysm, the device may be coated with a suitable thrombogenic agent, filled with a polyester fiber or woven polyester, or braided with an increased number of wire strands. The polyester fiber may attach to a clot to retain the clot firmly within the device as it forms the occlusion.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment site, such as immediately adjacent an aneurysm for example.

The medical device can be constrained into its reduced diameter configuration and inserted into the lumen of the catheter. The collapsed configuration of the device may be of any shape suitable for easy passage through the lumen of a catheter and proper deployment out the distal end of the catheter. For example, the device may have a relatively elongated collapsed configuration wherein the device is stretched along its axis. This collapsed configuration can be achieved simply by stretching the device generally along its axis, e.g., by manually grasping the ends of the device and pulling them apart, which will tend to collapse the expanded diameter portions of the device inwardly toward the device's axis. In this regard, these devices are not unlike "Chinese handcuffs", which tend to constrict in diameter under axial tension.

If the device is to be used to permanently exclude an aneurysm in a patient's body, for example, one can simply retract the delivery catheter while maintaining the position of the device, to deploy the device followed by disconnection and removal of the deployment device and catheter from the patient's body. This will leave the medical device deployed in the patient's vascular system so that it may exclude the aneurysm. In some circumstances, the medical device may be attached to a delivery system in such a manner as to secure the device to the end of the delivery device. Before removing the catheter in such a system, it may be necessary to detach the medical device from the delivery device before removing the catheter and the delivery device. By keeping the medical device attached to the delivery device, the operator can retract the device for repositioning relative to the abnormal opening, if it is determined that the device is not properly positioned. A delivery device attached to the medical device may allow the operator to control the manner in which the medical device is deployed out the distal end of the catheter.

Although the device will tend to resiliently return to its initial expanded configuration, i.e., its shape prior to being collapsed for passage through the catheter, it should be understood that it might not always return entirely to that shape. For example, it may be desirable that the device has a maximum outer diameter in its expanded configuration at least as large as and preferably larger than, the inner diameter of the opening in which it is to be deployed. For instance, the outer diameter of the device may be about 10-30% larger than the inner diameter of the opening. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat and retain the device therein.

When the device is deployed in a patient, thrombi will tend to collect on the surface of the strands. By having a greater strand density and smaller flow passages between strands as afforded by the multiple layer construction of the present invention, the total surface area of the strands and flow resistance will be increased, increasing the thrombotic activity of the device and permitting it to relatively rapidly restrict or shunt flow through the vessel in which it is deployed or in the case of a graft, occlude the wall of the stent graft to exclude an aneurysm, but not occlude the vessel.

The device may be delivered and properly placed using two dimensional ICE, MRI, transesophageal echocardiography, angiography, and/or Doppler color flow mapping. With the advent of two dimensional ICE, MRI, transesophageal echocardiography, bi-plane angiography, and Doppler color flow mapping, the approximate anatomy of the defect can be visualized. The device that is employed will be based on the approximate size of the vessel or abnormality in which the device is to be placed.

The delivery device employed may take any suitable shape, such as an elongate flexible metal shaft or hypotube or metal braided polymer tube configured to constrain the medical device. The delivery device can be used to urge the medical device through the lumen of a catheter/sheath for deployment in a channel of a patient's body. When the medical device is deployed out the distal end of the catheter, the delivery device may still retain it. As also explained in further detail below, the specific delivery method will depend on the particular device to be deployed within the body.

Referring now to the drawings, a discussion of the embodiments of various medical devices of the present invention will next be presented. FIG. 1 illustrates a first embodiment of a medical device 10 for treating a target site. For example, the medical device 10 could be a stent graft used for treating various body lumens, such as for treating an aneurysm. The medical device 10 includes an inner layer 12 and an outer layer 14 and at least one gap 16 defined therebetween. Thus, at least a portion of the inner 12 and outer 14 layers may be spaced apart from one another to define one or more gaps 16 therebetween. The gap(s) 16 may be defined over a majority of the outer surface of the inner layer 12 and the inner surface of the outer layer 14 (e.g., greater than about 50%). In addition, the gap(s) 16 between the layers may be various distances, such as 1-3 times the thickness of one layer. Thus, a substantial portion of the surface area of the adjacent layers may be separated from one another. As explained in further detail below, the one or more gaps 16 may be defined between the inner 12 and outer 14 layers in order to facilitate thrombosis between the layers. The gap(s) 16 would typically be positioned proximate to the target site to be treated, such as an aneurysm. Thus, the device 10 may be able to more quickly occlude a target site such as an aneurysm and facilitate blood flow between the proximal 18 and distal 20 ends of the device.

The inner 12 and outer layers 14 may be any suitable material capable of being positioned within a lumen for treating a target site, such as a braided fabric as discussed above. The inner layer 12 is disposed within the outer layer 14, and the inner and outer layers may be coaxial to one another. The inner 12 and outer 14 layers may be tubular in configuration and/or at least partially overlie one another. In addition, the inner 12 and outer 14 layers may be spaced apart from one another at various locations between the proximal 18 and distal 20 ends of the device 10 (see e.g., FIG. 10) or may be spaced apart from one another entirely between the proximal and distal ends of the device 10 (see e.g., FIG. 1). Furthermore, the inner 12 and outer 14 layers may be coupled together at various locations, such as with sutures approximately midway between the proximal 18 and distal 20 ends. The inner 12 and outer 14 layers may have similar expansion and elongation characteristics such that the layers collapse together for delivery through a catheter as explained in further detail below.

According to exemplary embodiments of the present invention, the gaps 16 may be defined via one or more offsets 22 located between the inner 12 and outer 14 layers, such as rings, tubes, or similar spacers capable of spacing at least a portion of the inner and outer layers away from one another. The offsets 22 may alternatively be defined as radial surface distortions in the inner layer 12 and/or the outer layer 14, such as one or more dimples, radial or annular ridges, corrugations, flutes, or other desired surface distortions. The offsets 22 may be integrally formed in the inner 12 and/or outer 14 layers and heat set into a desired shape as described above. The offsets are configured to define one or more gaps 16 between the inner 12 and outer 14 layers such that a majority of the surface area between the inner and outer layers is spaced apart. The offsets 22 may be defined longitudinally, circumferentially, spirally, or in any other desired configuration. Any number of desired offsets 22 may be located between the proximal 18 and distal 20 ends of the inner 12 and outer 14 layers. Moreover, according to one embodiment, there may be no gaps at the proximal 18 and/or distal 20 ends, such as shown in FIG. 6, which may provide a better seal against the vessel wall on either side of the aneurysm and apply uniform outward pressure against the vessel wall for anchoring as compared to surface distortions that may cause localized higher pressure points. Additionally, one of the inner and outer layers may be longer than the other of the inner and outer layers and flare outward at the ends or evert at the ends to aid in sealing against the vessel wall.

For instance, FIG. 2 illustrates one embodiment where a plurality of offsets 22 are positioned between the inner 12 and outer 14 layers and are employed to keep at least a portion of the inner 12 and outer 14 layers spaced apart from one another to define the gap(s) 16. The offsets 22 may have an annular ring configuration 24 as shown in FIG. 3 and be disposed between the inner and outer layers and spaced axially from one another along the longitudinal axis between the proximal 18 and distal 20 ends of the device. The outer diameter of each offset 22 may be about the same as the inner diameter of the outer layer 14, while the inner diameter of the offset 22 may be about the same as the outer diameter of the inner layer 12. Thus, the size of the offset 22 may vary depending on the sizes of the inner 12 and outer 14 layers. However, the offsets 22 may be other configurations capable of defining a gap 16 between the inner 12 and outer 14 layers, such as any spacer capable of being positioned between, and at least partially about the circumference of, the inner and outer layers. For example, the width of each offset 22 may vary depending on the size and number of gaps 16 desired. The number of offsets 22 may vary depending on the number of gaps 16 desired and the amount of support needed to keep the inner 12 and outer 14 layers spaced apart from one another. According to exemplary embodiments, the offset 22 may be a sponge material, such as a collapsible open cell foam of a number of biocompatible polymeric materials, or may be a collapsible tube, such as a thin wall collapsible tubular member made from a biocompatible polymer or elastomer material.

Additional embodiments are illustrated in FIGS. 4 and 5, wherein a plurality of tubes 26 are disposed between the inner 12 and outer 14 layers. The tubes may be collapsible for delivery through a catheter and may be made of metallic or non-metallic materials, such as a polymeric or elastomeric open cell foam or a braided polymer or metallic filament tubular member or a solid member and may have similar elongation characteristics as the inner and/or outer layers. Tubes 26 may be configured to occlude the flow of blood therethrough if desired such that the tubes could be an occlusive material or include one or more planes of occlusion transverse to the flow of blood. The tubes 26 may have a constant diameter along their length (e.g., cylindrical in configuration) or may have a varying diameter (e.g., a Venturi tube configuration). As before, the sizes of the tubes 26 may vary depending on the sizing and relative spacing between the inner 12 and outer 14 layers. FIG. 4 shows one embodiment where a plurality of discontinuous tubes 26 are spaced apart from one another to define a gap therebetween. The tubes 26 are disposed generally parallel to the longitudinal axis of the device 10, and there may be any number of tubes in a variety of positions. In particular, FIG. 5 shows one embodiment where four tubes are spaced equidistantly about the circumference of the inner 12 and outer 14 layers.

FIGS. 7-10 illustrate additional embodiments of offsets that may be employed to define gaps 16 between the inner 12 and outer 14 layers. Namely, FIGS. 7 and 8 illustrate embodiments where a plurality of external flutes 32 are defined on the outer surface of the inner layer 12. The external flutes 32 project from the outer surface of the inner layer 12 such that gaps 16 are defined on opposite sides of each external flute. The external flutes 32 could extend helically (see e.g., FIG. 7) or annularly (see e.g., FIG. 8) about the inner layer 12, but may also extend longitudinally along the length of the inner layer if desired. The gaps 16 may also be defined by a plurality of internal flutes 34 as shown in FIG. 9. The internal flutes 34 project inwardly within the outer surface of the inner layer 12 to define a gap 16 between each internal flute and the outer layer 14. Similar to the external flutes 32, the internal flutes 34 may extend annularly about the inner layer 12 as shown in FIG. 9 or may alternatively extend helically or longitudinally along the length of the device 10. FIG. 10 depicts a further embodiment of the present invention, wherein the inner layer 12 includes a corrugated surface having a plurality of corrugations 36 extending along its length. Thus, when the inner layer 12 is positioned within the outer layer 14 in an overlying relationship, gaps 16 may be defined on opposite sides of each corrugation 36. The frequency and size of the corrugations 36 may vary depending on the sizes of the inner 12 and outer 14 layers, and each corrugation may extend annularly about the inner layer. It should be noted that all offsets depicted as projections of the outer surface of the inner layer 12 may alternatively be inward projections of the outer surface or may be projections of both the outer surface inward and the inner surface outward. In addition, the projections of one layer may contact projections from the other layer to create a gap between surfaces of the inner and outer layers. For example the inner layer 12 may have an outwardly directed spiral flute in one helical direction that meets an oppositely inwardly directed helical spiral flute in the outer layer 14 that has an opposite helical direction wherein the flutes cooperate to space the layers apart over a majority of their adjacent surfaces.

FIGS. 11 and 12 illustrate additional embodiments of the present invention. In this regard, FIG. 11 depicts an inner layer 12 having a plurality of T-shaped surface distortions to define a plurality of gaps 16 between the inner 12 and outer 14 layers. The gaps 16 may be formed between the inner and/or outer surface of the inner layer 12 and the inner surface of the outer layer 14. Alternatively, FIG. 12 shows that the inner layer 12 may have undulating surface distortions defined about its circumference to define a plurality of gaps 16 between the inner and outer 14 layers. In both FIGS. 11 and 12, the gaps 16 extend longitudinally along the axis of the inner 12 and outer 14 layers, and the gaps could extend the entire length of each layer or some portion therebetween.

FIG. 13 illustrates another embodiment where the inner layer 12 is everted within the outer layer 14. Thus, the inner 12 and outer 14 layers may be formed from the same tubular member, while a portion of the tubular member may include a corrugated surface or other surface distortions such that when the inner layer is everted within the outer layer, the corrugations define gaps 16 therebetween. Yet another embodiment is shown in FIG. 14 where an end 38 of the inner layer 12 is everted or rolled over within the outer layer 14 to define a gap 16 therebetween. In addition, a portion of the inner layer may include a corrugated surface or other surface distortions such that additional gaps 16 may be defined between the inner 12 and outer 14 layers.

In use, the medical device 10 would be delivered within a catheter 40 at a diameter that is smaller than its heat set diameter such as shown in FIG. 15. Typically, the medical device 10 would be constrained, such as by axially elongating the medical device to a smaller diameter and positioning the distal end of the fabric wires within a catheter 40 for delivery to a target site. The proximal end 18 of the medical device 10 may be engaged by a delivery device 42 as also shown in FIG. 15. The catheter 40, medical device 10, and delivery device 42, would be introduced into the patient together such as, for example, through an introducer sheath and placed using the Seldinger technique to gain vascular access (e.g., through the femoral artery). The medical device 10 may then be guided through the vascular system until a distal end of the catheter 40 is proximate to a target site to be treated. With the medical device 10 and the delivery device 42 held stationary, the catheter 40 is withdrawn in the proximal direction to partially eject the medical device from the distal end of the catheter until the medical device is released and self-expands to engage the lumen. The natural tendency of the medical device 10 is to return to the expanded heat set configuration once released from the catheter 40. When the medical device 10 is fully deployed from the catheter 40, the delivery device 42 may disengage the proximal end 18 of the medical device 10 and allow the proximal end of the device to self expand. According to one embodiment, the medical device 10 may be positioned within a lumen to bridge or exclude an aneurysm, with the medical device engaging the lumen upstream and downstream of the aneurysm. For further exemplary details regarding techniques for delivering the medical device, Applicants hereby incorporate U.S. Patent Appl. Publ. No. 2006/0253184, filed May 4, 2005 and U.S. Patent Appl. Publ. No. 2007/0118207A1, filed Jan. 17, 2007, herein in their entirety.

FIG. 16 illustrates an additional embodiment for delivering the medical device 10 wherein the inner 12 and outer 14 layers are delivered separately but in the same catheter 40. The inner 12 and outer 14 layers may be delivered coaxially with one another within the catheter 40. Thus, the inner 12 and outer 14 layers may be configured to be separated for delivery within a catheter 40. In addition, the inner 12 and outer 14 layers could be formed from a single layer of material and inverted with respect to one another into an overlying relationship or may be completely independent from one another and delivered separately within the same catheter 40. According to one embodiment where the inner 12 and outer 14 layers are delivered independently, one or more offsets may be formed in both surfaces such that the offsets may prevent axial relative movement between the layers after the inner layer is deployed within the outer layer. For example, each of the inner 12 and outer 14 layers may have radial rings in axial positions that lie against each other to prevent or limit axial movement. For an embodiment wherein the medical device 10 is formed from a single tubular member, the medical device may include two or more layers arranged as a single layer in the catheter, such as a three layer device having a middle layer between the inner 12 and outer 14 layers and formed from a single tubular member where the middle layer has corrugations or other offset shapes to serve as the spacer between the inner and outer layers.

Although the natural tendency of the medical device 10 is to return to the expanded heat set configuration, once released from the catheter, some intervention by the physician may be necessary in order to position the inner layer 12 within the outer layer 14 when the inner and outer layer are fabricated from one tubular member. Once the outer layer 14 of the medical device 10 is deployed, the physician may then urge the delivery device 42 and or catheter 40 distally so as to force the medical device to invert within itself to initially begin the formation of inner layer 12. Distal advancement of the delivery device 42 and/or proximal retraction of the catheter 40 may result in deploying the inner layer 12 as the layer returns to its heat set configuration. When delivered separately, the outer layer 14 may be delivered at the target site first, and then the catheter 40 and delivery device 42 may be advanced into the lumen of the outer layer so that the distal ends of the inner and outer layers align, and then the inner layer may be deployed by retracting the catheter and disengaging the delivery device.

Embodiments of the present invention may provide several advantages. For example, the medical device may be a stent graft capable of more effectively excluding an aneurysm. In particular, the medical device may include one or more gaps that facilitate thrombosis by creating a turbulent boundary layer between and around the inner and outer layers in order to create and trap thrombus in the gaps. The gaps may be defined using a variety of techniques, such as one or more offsets located between the inner and outer layers or formed into the surface of one or more adjacent layers, that may be customizable for different target sites. In addition, the medical device may be delivered using various techniques, including delivering the inner and outer layers separately, such that the medical device may be delivered within a catheter having a smaller inner diameter than multi-layered medical devices that may not otherwise be capable of being delivered separately. Moreover, the medical device may be used to exclude, occlude, shunt, or restrict flow in vessels, channels, lumens, cavities, or organs anywhere in the vasculature or body.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device for treating a vascular abnormality in a lumen, the medical device comprising:
a multi-layered structure comprising an inner layer disposed within an outer layer and having proximal and distal ends, wherein the inner layer is a first fabric comprising a plurality of braided strands comprising an elastic metallic alloy and the outer layer is a second fabric comprising a plurality of braided strands, the first fabric being discrete from the second fabric, each of the inner and outer layers having a respective longitudinal opening extending between the proximal and distal ends so as to define respective inner and outer surfaces, wherein the multi-layered structure further comprises at least one offset comprising a surface distortion formed helically or annularly in only one of the inner or outer layers, the at least one offset extending between the outer surface of the inner layer and the inner surface of the outer layer to define a gap between the inner and outer layers, wherein a majority of the outer surface of the inner layer is spaced apart from the inner surface of the outer layer by the at least one offset, and wherein the multi-layered structure is configured to be deployed within the lumen such that at least a portion of the outer surface of the outer layer is configured to engage an inner surface of the lumen and the at least one gap is configured to allow blood flow therethrough so as to promote thrombosis between the inner and outer layers.

2. The medical device of claim 1, wherein the inner and outer layers comprise an occlusive material.

3. The medical device of claim 1, wherein the braided strands of the outer layer comprises a non-metallic material.

4. The medical device of claim 1, wherein the outer layer comprises braided strands of an elastic metallic alloy.

5. The medical device of claim 1, wherein the multi-layered structure comprises an expanded heat set configuration, and wherein the multi-layered structure is configured to be constrained to a smaller diameter than the expanded heat set configuration for delivery within a catheter.

6. The medical device of claim 1, wherein each of the inner and outer layers is tubular in configuration, and wherein the inner layer is coaxially disposed within the outer layer.

7. The medical device of claim 1, further comprising a plurality of gaps defined between the proximal and distal ends of the multi-layered structure.

8. The medical device of claim 1, wherein the at least one surface distortion is the shape of a corrugation formed on only one of the outer surface of the inner layer or the inner surface of the outer layer.

9. The medical device of claim 1, wherein the at least one surface distortion comprises a flute formed on only one of the outer surface of the inner layer or the inner surface of the outer layer.

10. The medical device of claim 1, further comprising a plurality of offsets formed in only one of the inner or outer layer.

11. The medical device of claim 10, wherein the plurality of offsets comprise surface distortions formed in only one of the inner or outer layers, and wherein the inner layer is disposed within the outer layer in an overlying relationship so as to define a plurality of gaps therebetween.

12. The medical device of claim 1, wherein the medical device further comprises occlusive material disposed within at least a portion of the gap between the inner and outer layers.

13. The medical device of claim 1, wherein the multi-layered structure is a stent graft configured to engage the lumen upstream and downstream of an aneurysm.

14. The medical device of claim 1, wherein the at least one gap is configured to increase turbulence of blood flow in and around the gap so as to promote thrombosis between the inner and outer layers whereby blood flow within the gap is eliminated.

15. The medical device of claim 1, wherein the at least one offset is formed in the outer surface of the inner layer.

16. The medical device of claim 1, wherein the at least one offset is defined in the inner layer.

17. The medical device of claim 1, wherein the at least one offset is formed in the inner surface of the outer layer.

18. The medical device of claim 1, wherein the inner layer comprises a braided tubular surface having a first outer diameter, and wherein the at least one offset projects from the braided tubular surface to define a second outer diameter different than the first outer diameter.

19. A medical device for treating a vascular abnormality, comprising:
a tubular shaped inner layer, comprising:
proximal and distal ends;
a first fabric comprising a plurality of braided strands comprising an elastic metallic alloy; and
inner and outer surfaces;
a tubular shaped outer layer, comprising:
proximal and distal ends;
a second fabric comprising a plurality of braided strands; and
inner and outer surfaces; and
at least one offset feature extending between the outer surface of the inner layer and the inner surface of the outer layer to form at least one gap to accommodate blood flow between the outer and inner layers, the at least one offset feature being formed helically or annularly from only one of the inner and outer layers, wherein the medical device is configured to be deployed within a lumen such that at least a portion of the outer surface of the outer layer is configured to engage an inner surface of the lumen.

20. The medical device of claim 19, wherein the at least one offset feature comprises a corrugation formed on only one of the outer surface of the inner layer or the inner surface of the outer layer.

21. The medical device of claim 19, wherein the at least one offset feature comprises a flute formed on only one of the outer surface of the inner layer or the inner surface of the outer layer.

22. The medical device of claim 19, wherein the at least one offset feature is formed only in the inner layer.

* * * * *